(12) United States Patent
Knowlen et al.

(10) Patent No.: US 10,384,180 B2
(45) Date of Patent: Aug. 20, 2019

(54) SUPERSONIC SHOCK WAVE REACTORS, AND ASSOCIATED SYSTEMS AND METHODS

(71) Applicants: University of Washington through its Center for Commercialization, Seattle, WA (US); UOP LLC, Des Plaines, IL (US)

(72) Inventors: Carl Knowlen, Seattle, WA (US); Arthur T. Mattick, Seattle, WA (US); Carl J. Stevens, Lake Forest, IL (US); Robert Cerff, Seattle, WA (US); Viggo Hansen, Seattle, WA (US)

(73) Assignee: University of Washington, Seattle, WA (US)

( * ) Notice: Subject to any disclaimer, the term of this patent is extended or adjusted under 35 U.S.C. 154(b) by 504 days.

(21) Appl. No.: 15/034,863

(22) PCT Filed: Nov. 19, 2014

(86) PCT No.: PCT/US2014/066407
§ 371 (c)(1),
(2) Date: May 5, 2016

(87) PCT Pub. No.: WO2015/077335
PCT Pub. Date: May 28, 2015

(65) Prior Publication Data
US 2016/0296904 A1 Oct. 13, 2016

Related U.S. Application Data

(60) Provisional application No. 61/906,353, filed on Nov. 19, 2013.

(51) Int. Cl.
*B01J 7/00* (2006.01)
*C07C 2/78* (2006.01)
(Continued)

(52) U.S. Cl.
CPC ............... *B01J 7/00* (2013.01); *B01J 12/00* (2013.01); *B01J 12/005* (2013.01); *B01J 19/10* (2013.01);
(Continued)

(58) Field of Classification Search
CPC ... B01J 7/00; B01J 12/00; B01J 12/005; B01J 19/26; B01J 19/10; B01J 2219/0883;
(Continued)

(56) References Cited

U.S. PATENT DOCUMENTS 3,839,618 A * 10/1974 Muehlberger .......... B05B 7/168
219/121.47
4,724,272 A 2/1988 Raniere et al.
(Continued)

FOREIGN PATENT DOCUMENTS

EP 1413354 A1 4/2004
RU 2100066 C1 12/1997
(Continued)

OTHER PUBLICATIONS

Eurasian Search Report received in Eurasian Patent Application No. 201691041.
(Continued)

*Primary Examiner* — Nicholas A Smith
*Assistant Examiner* — Colleen M Raphael
(74) *Attorney, Agent, or Firm* — Perkins Coie LLP (57) ABSTRACT

Apparatuses and associated methods for forming olefins from saturated hydrocarbon feedstock are disclosed herein. In one embodiment, a carrier gas is introduced at a supersonic velocity to a feedstock injector section. A feedstock gas is introduced to the carrier gas stream using feedstock injectors that are offset in the streamwise direction one from another. The upstream feedstock injectors are positioned to inject feedstock gas to create plumes that improve penetra-
(Continued)

tion depth of the feedstock gas and reduce pressure losses at the downstream feedstock injectors. The feedstock gas can be regeneratively preheated by cooling the convergent-divergent nozzle. Water, steam and/or hydrogen gas can be injected into the apparatus for cooling the throat of the convergent-divergent nozzle.

33 Claims, 6 Drawing Sheets (51) Int. Cl.
  *B01J 12/00*   (2006.01)
  *B01J 19/10*   (2006.01)
  *B01J 19/26*   (2006.01)
  *C07C 11/24*   (2006.01)
  *C10G 15/08*   (2006.01)
  *C10G 31/06*   (2006.01)

(52) U.S. Cl.
  CPC ............ *B01J 19/26* (2013.01); *C07C 2/78* (2013.01); *C10G 15/08* (2013.01); *C10G 31/06* (2013.01); *B01J 2219/00087* (2013.01); *B01J 2219/00123* (2013.01); *B01J 2219/00135* (2013.01); *B01J 2219/00159* (2013.01); *B01J 2219/0218* (2013.01); *B01J 2219/0883* (2013.01)

(58) Field of Classification Search
  CPC .... B01J 2219/00135; B01J 2219/00123; B01J 2219/00087; B01J 2219/0218; B01J 2219/00159; C10G 15/08; C10G 31/06
  See application file for complete search history.

(56) References Cited

U.S. PATENT DOCUMENTS

| | | | |
|---|---|---|---|
| 2012/0270275 A1* | 10/2012 | Fenton | C12M 21/12 435/99 |
| 2014/0056770 A1* | 2/2014 | Bedard | B01J 19/02 422/128 |
| 2014/0058149 A1 | 2/2014 | Negiz et al. | |
| 2014/0058162 A1* | 2/2014 | Negiz | B01J 19/02 585/539 |
| 2014/0058179 A1 | 2/2014 | Stevens et al. | |
| 2014/0121346 A1* | 5/2014 | Tang | B01J 19/10 422/128 |
| 2014/0216405 A1* | 8/2014 | Kato | F02M 53/02 123/445 |

FOREIGN PATENT DOCUMENTS

| | | |
|---|---|---|
| RU | 2371246 C2 | 10/2009 |
| WO | 2014031288 A1 | 2/2014 |
| WO | 2014031431 A1 | 2/2014 |
| WO | 2014070419 A2 | 5/2014 |
| WO | 2014210297 A1 | 12/2014 |

OTHER PUBLICATIONS

Exam Report dated Jun. 5, 2017 in Canadian Application No. 2930838, 5 pages.
Examination Report dated Dec. 22, 2016 in corresponding Australian Patent Application No. 2014353052, 5 pages.

\* cited by examiner

SUPERSONIC SHOCK WAVE REACTORS, AND ASSOCIATED SYSTEMS AND METHODS

TECHNICAL FIELD

The present technology relates generally to supersonic shock wave reactors suitable for olefin hydrocarbon formation. In particular, several embodiments of the present technology are directed to producing olefin products by passing feedstock and carrier gases through controlled shock waves.

BACKGROUND

Olefins are unsaturated open hydrocarbons, i.e., hydrocarbons having at least some double or triple carbon-to-carbon bonds. Examples of olefins having double carbon-to-carbon bond include ethylene ($C_2H_4$) and propylene ($C_3H_6$). Acetylene ($C_2H_2$) is an example of an olefin having a triple carbon-to-carbon bond. Conventional methods for manufacturing olefins include cracking from crude oil. For example, longer hydrocarbon chains having single carbon-to-carbon bonds (i.e., saturated hydrocarbons) and/or cyclical hydrocarbons can be synthesized into shorter hydrocarbon chains with double carbon-to-carbon bonds under high temperatures in presence of steam. The temperature needed to sustain this reaction may reach 1200 K. Additionally, the conventional cracking process requires good process control because if the product temperature or residence time is excessive, undesired carbon deposits may form on the equipment. Conversely, if the product temperature is too low or residence time is too short, the conversion to the olefins is incomplete, thereby reducing the efficiency of the cracking.

Figure 1:
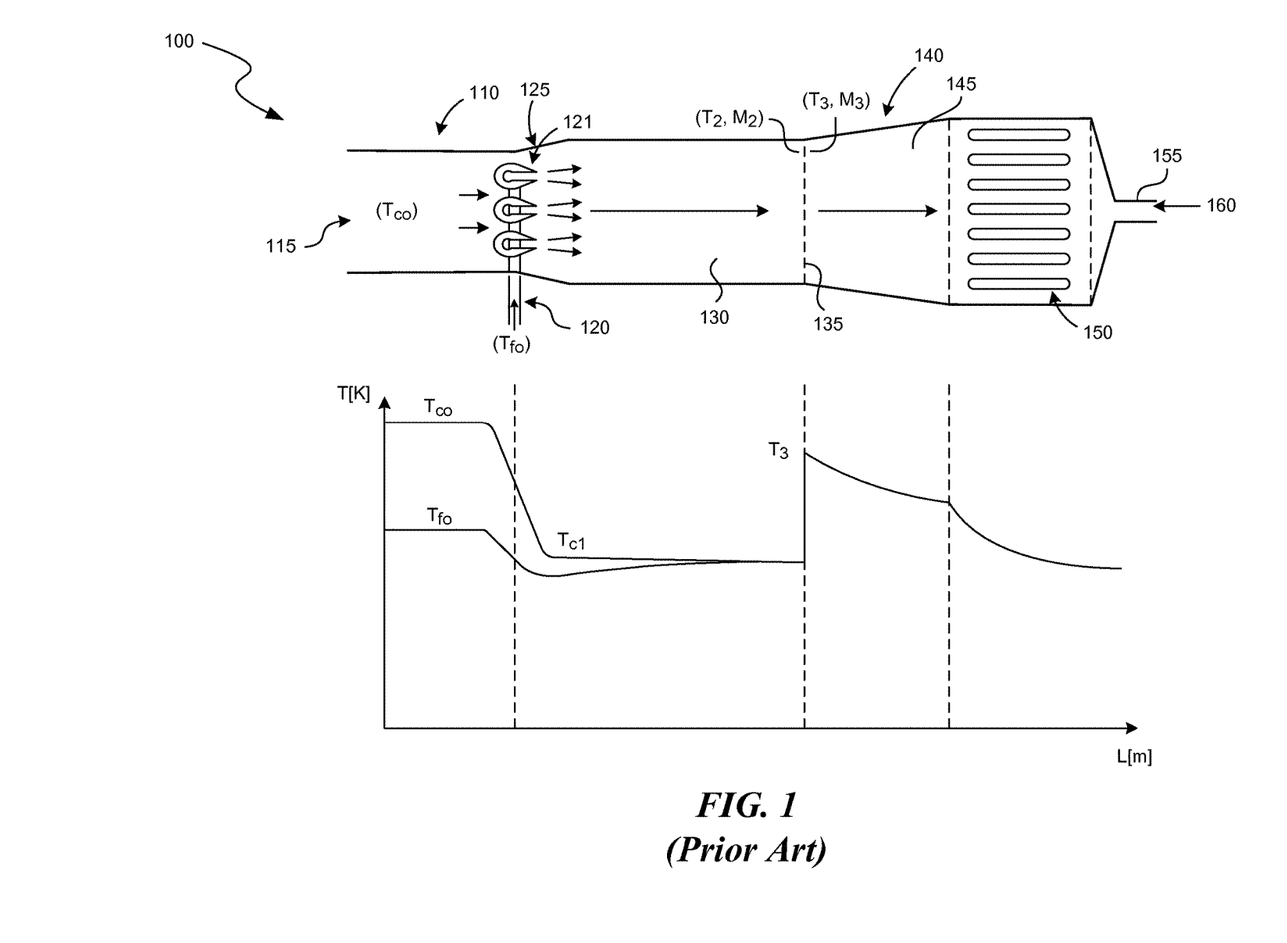
FIG. 1 is a partial schematic view of a shock wave reactor for producing olefins configured in accordance with the prior art.

FIG. 1 illustrates a shock wave olefin reactor 100 configured in accordance with the prior art and the accompanying temperature graph of the gases in the reactor. The shock wave reactor 100 is suitable for manufacturing olefins by synthesizing feedstock gas (e.g., removing the hydrogen atoms from the feedstock gas). In the illustrated process, a high temperature carrier gas (e.g., steam at temperature $T_{co}$) is fed at an entrance 115 of a subsonic section 110. A feedstock gas 120 (e.g., having hydrocarbons with single carbon-to-carbon bonds or methane ($CH_4$)) is added at some downstream distance from the entrance 115 through nozzles 121 at temperature $T_{fo}$ that is smaller than $T_{co}$. A mixture of carrier gas and feedstock gas expands and accelerates through a diffuser section 125. The carrier gas 115 and the feedstock gas 120 further mix as they travel through a mixing section 130 toward a shock wave location 135. Upstream of the shock wave location 135, flow of the carrier gas/feedstock gas mixture is supersonic, while the flow of the carrier gas/feedstock gas mixture downstream of the shock wave location 135 is subsonic. The transition from supersonic conditions ($T_2$, $M_2$) to subsonic conditions ($T_3$, $M_3$) is accompanied by a rapid temperature rise in the mixture, which promotes conversion from methane and/or the hydrocarbons having single carbon-to-carbon bonds to hydrocarbons having at least some double or triple carbon-to-carbon bonds. The hydrocarbons continue to rapidly react in a section 145 downstream of the shock wave location 135 due to a relatively high temperature in this section. Further downstream, the olefins enter a heat exchanger 150 where they are cooled down to a lower temperature. The olefins, the remaining unreacted hydrocarbons, and other products of reaction (e.g., carrier gas, carbon) exit the reactor 100 at an outlet 155 as a stream 160.

This conventional process, however, suffers from several shortcomings. For example, the nozzles 121 in the stream of carrier gas can overheat and can also cause undesirable pressure losses in the carrier gas. Mixing of the feedstock gas and the carrier gas may be incomplete when the mixture arrives to the shock wave location 135. Furthermore, rapid temperature increase across the shock wave location 135 is difficult to control and may cause overheating or underheating of the feedstock gas. Such overheating/underheating may result in carbonization or incomplete reaction of the feedstock gases.

DETAILED DESCRIPTION

The present technology relates generally to producing olefin products by passing feedstock and carrier gases through controlled shock waves. In particular, some examples of the present technology are directed toward apparatuses and methods for making olefins from feedstock gas that is methane and/or hydrocarbons with single carbon-to-carbon bonds. As used herein, the term "olefins" denotes hydrocarbons having double or triple carbon-to-carbon bonds. Other terms that denote such hydrocarbons are "olefinically unsaturated" and/or "acetylinic." Unless otherwise noted, the term olefin is used herein to encompass these terminology variations. In some embodiments, a high temperature carrier gas can be prepared by igniting a mixture of fuel (e.g., methane or hydrogen) and oxidizer (e.g., oxygen). The feedstock gas containing hydrocarbons can be introduced into and mixed with a stream of the carrier gas. The carrier gas at high temperature can provide enthalpy needed for synthesizing the feedstock gas into olefins. Furthermore, the presence of the carrier gas in the mixture reduces the partial pressure of the feedstock gas which, in at least some embodiments, promotes synthesis of the feedstock gas into olefins. In at least some embodiments, the synthesis of the feedstock gas into olefins is pyrolitic, i.e., performed at elevated temperature in the absence of free oxygen.

Some embodiments of the present technology are directed to improving the aerodynamics of the feedstock gas introduction, resulting in reduced pressure losses as the feedstock gas enters the stream of the carrier gas and mixes with the carrier gas at high temperature. For example, the feedstock gas can be introduced in a feedstock injector section of the reactor through a series of feedstock injectors distributed at different streamwise locations. The more upstream feedstock injectors create plumes that are swept to the vicinity of the downstream feedstock injectors. The presence of the plumes is expected to reduce pressure losses and improve mixing of the feedstock gas and the carrier gas. Such aerodynamic introduction of the feedstock gas is also expected to reduce the strength of the shock waves typically associated with mixing supersonic streams. The feedstock gas may approach the thermal cracking (e.g., olefin-creating or olefin-synthesizing) temperature while passing through a series of oblique shock waves in the feedstock injector section. Downstream of the feedstock injector section, the feedstock gas flows through a supersonic feedstock mixer section and further toward a supersonic diffuser section where the feedstock gas undergoes a controlled thermal cracking. In at least some embodiments of the present technology, the contracting section of the supersonic diffuser section balances a rise in temperature associated with deceleration of the gases (at supersonic velocity gases decelerate as they experience contraction) with a reduction in temperature associated with the pyrolitic reaction (pyrolitic reaction lowers the temperature of the gases because the reaction is endothermic). The balance of these two opposing effects results in a generally isothermal flow of the gases flowing through the supersonic mixer section. The normal shock wave train in the expanding section of the supersonic diffuser decelerates the resulting mixture of carrier gas, feedstock, and olefins from a supersonic flow to a subsonic flow. The concomitant increase in flow temperature enables the unreacted feedstock gas to undergo a pyrolitic reaction to create olefins. The olefins, carrier gas, and any remaining feedstock gas flow toward an outlet of the apparatus, and further toward a heat exchanger that can reduce the temperature of the mixture to arrest the high temperature chemical reactions (e.g., olefin-creating or olefin-decomposing reactions).

In some embodiments, the convergent-divergent nozzle that accelerates the subsonic carrier gas to a supersonic velocity can be cooled using feedstock gas, oxidizer, fuel, water and/or steam. The cooling, for example, can be regenerative cooling (e.g., preheating the feedstock gas, followed by routing the feedstock gas in the mixer section through the nozzle injector) and/or film cooling (e.g., a film of water that rapidly evaporates and cools the throat of the nozzle and then enters the feedstock injector section). In some embodiments, liner materials can be used to eliminate catalytic wall effects of for example, the stainless steel wall of the reactor.

Specific details of certain embodiments of the technology are set forth in the following description and in FIGS. 2-7 to provide a thorough understanding of such embodiments. One skilled in the art, however, will recognize that the technology can be practiced without one or more specific details explained in the following description. Moreover, although the following disclosure sets forth several embodiments of the technology, other embodiments of the technology can have different configurations or different components than those described in this section. As such, it should be understood that the technology may have other embodiments with additional elements or without several of the elements shown and described below with reference to FIGS. 2-7.

Figure 2:
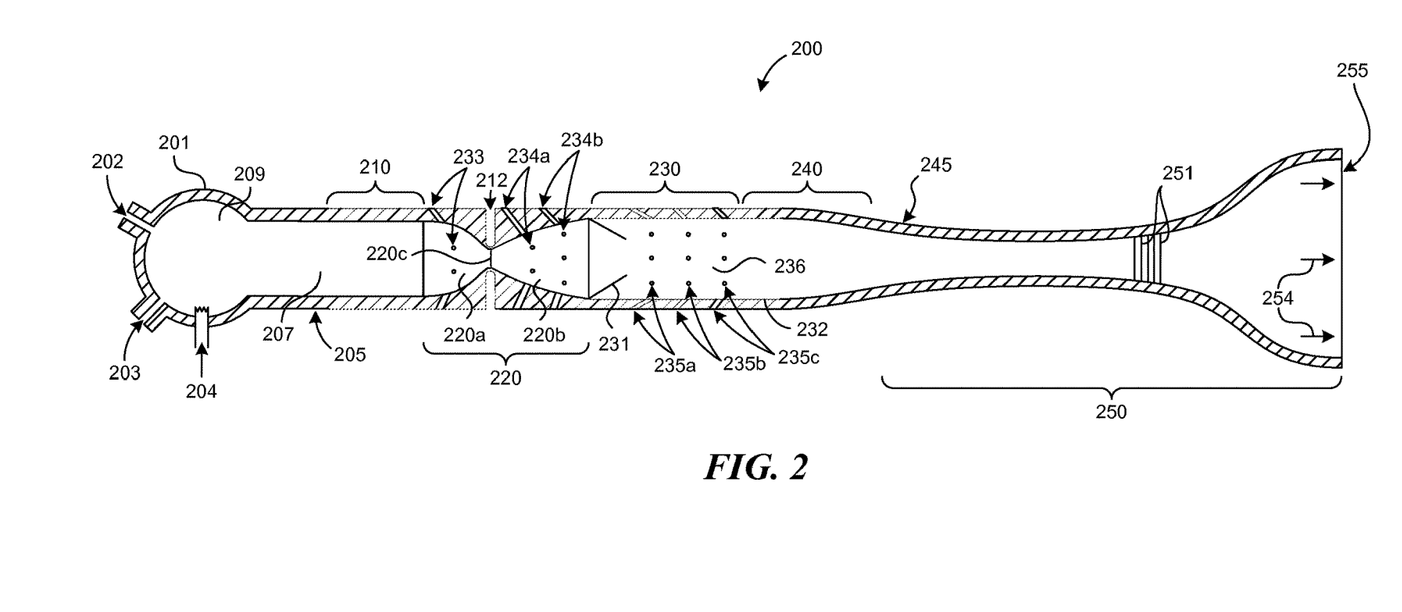
FIG. 2 is a partial schematic cross-sectional view of a supersonic reactor for producing olefins configured in accordance with an embodiment of the present technology.

FIG. 2, for example, is a partial schematic cross-sectional view of a supersonic shock wave olefin reactor 200 configured in accordance with an embodiment of the present technology. The flow of gases is generally left to right in the drawing. Briefly, and as described in greater detail below, a carrier gas 209 is generated in a carrier gas generator 201. A feedstock gas 236 is mixed with the carrier gas 209 in a feedstock injector section 230. The pyrolytic reaction continues through a supersonic mixer section 240 and through a supersonic diffuser section 250, resulting in a stream of olefins 254 at a diffuser outlet 255.

The reactor 200 in the embodiment illustrated in FIG. 2 includes the carrier gas generator 201 having a fuel inlet 202 and an oxidizer inlet 203. A chemical reaction can be initiated using an ignition device 204 to produce the carrier gas 209 from a mixture of fuel and oxidizer in the carrier gas generator 201. In some embodiments, the ignition device 204 can be a platinum wire at high temperature, a spark plug, a glow plug, or a device that injects small quantities of ether and oxygen which auto-ignite upon mixing at about 200° C. or higher temperature. The process of generating the carrier gas 209 is typically self-sustaining, requiring no additional external heat input to sustain the reaction once it has been started. In some embodiments, the fuel and oxidizer can be independently preheated to high temperatures such that the reaction between the fuel and oxidizer starts without any ignition device (i.e., the reaction is auto-ignited). In at least some embodiments, the fuel can be methane and/or hydrogen, and the oxidizer can be oxygen. For example, a combination of hydrogen fuel and oxygen oxidizer produces high temperature steam as the carrier gas 209. Other combinations of fuel and oxidizer are also possible. In some embodiments, the temperature of the carrier gas can reach up to 3300-3600 K. A relatively high temperature of the carrier gas provides enthalpy required for pyrolytic conversion of the feedstock gas hydrocarbons to the olefins having double and/or triple carbon-to-carbon bonds.

Downstream of a carrier gas feed section 210, the carrier gas 209 accelerates through a convergent-divergent nozzle 220 from (a) a subsonic velocity at the inlet of the nozzle 220 to (b) a supersonic velocity at the outlet. The convergent-divergent nozzle 220 is subjected to high heat load due to high temperature of the carrier gas 209. A throat 220$c$ of the nozzle 220 (downstream of a convergent section 220$a$ and upstream of a divergent section 220$b$) is subjected to especially high thermal loads from the carrier gas 209. In some embodiments, the convergent-divergent nozzle 220 can be cooled by injecting a film of cooling fluid through one or more cooling film injectors 233. Some examples of cooling fluid include water, steam, and hydrogen. After cooling the convergent-divergent nozzle 220, the cooling fluid travels downstream and mixes with the carrier gas. When water is used as the cooling fluid, it can rapidly evaporate at the throat 220$c$ and enter the carrier gas flow as superheated steam. In some embodiments, use of hydrogen as a cooling fluid is expected to improve pyrolysis in the downstream. Convergent shock waves 231 may exist at a transition from the convergent-divergent nozzle 220 to the feedstock injector section 230. In some embodiments, the transition may be designed to minimize the convergent shock waves 231.

In some embodiments of the present technology, the feedstock injector section 230 may receive the carrier gas 209 at a supersonic speed. The feedstock injector section 230 can have one or more feedstock injectors 235 (three are shown in FIG. 2 as feedstock injectors 235$a$-235$c$) configured to introduce the feedstock gas 236 to the olefin reactor 200. The feedstock gas can include, for example, methane ($CH_4$), ethane ($C_2H_6$), propane ($C_3H_8$) and/or other saturated hydrocarbons. In some embodiments, the feedstock injectors 235$a$-235$c$ can be distributed at several streamwise locations along the reactor 200. For example, upstream feedstock injectors 235$a$ can introduce the feedstock gas into the supersonic flow of the carrier gas 209, creating plumes that are swept toward the downstream feedstock injectors 235b and The presence of the plumes at the downstream feedstock injectors are expected to reduce pressure losses and to increase penetration depth of the feedstock gas away from the walls of the apparatus as the feedstock gas enters the flow. The plumes can also improve mixing of the feedstock and carrier gases. In some embodiments, the weaker shock waves at the downstream feedstock injectors 235b and 235c may also minimize premature temperature rise of the feedstock gas, which generally promotes formation of the undesirable precursor species (e.g., carbon). In some embodiments, about 50% of total effluent (i.e., total gas flow through the reactor) may be introduced through the feedstock injectors 235a-235c, corresponding to about 1:1 ratio of the feedstock to carrier gas flows. In other embodiments, the ratio of the feedstock to carrier gas flows may be about 0.5 or 0.75, but other ratios are also possible.

In some embodiments, a portion of the feedstock gas can be routed around the throat 220c of the convergent-divergent nozzle 220 before entering the feedstock injectors 235a-235c, thus preheating the feedstock gas while cooling the throat 220c. Transferring waste heat from the throat 220c back into the process is expected to help improve the overall efficiency of the process. Additionally or instead of introducing the feedstock gas through the feedstock injectors 235a-235c, in some embodiments the feedstock gas may be introduced through the nozzle injectors 234a-234b of the convergent-divergent nozzle 220. This arrangement is expected to reduce overall pressure losses because the supersonic flow is not vet fully expanded and fully accelerated to its ultimate supersonic velocity at the location of the nozzle injectors 234a-234b (i.e., the Mach number is lower in the convergent-divergent nozzle 220 than in the feedstock injector section 230).

At a relatively high temperature of the mixture of carrier/feedstock gases, some metals (e.g., Ni, Fe, Fe oxides, etc.), catalyze creation of carbon from the feedstock gas. Carbon is generally an undesired byproduct of the process. Therefore, in at least some embodiments, a liner 232 can he applied over at least a portion of an inner wall of the olefin reactor 200 to reduce or eliminate undesired catalytic reactions. In some embodiments, for example, the liner 232 may be composed of high temperature ceramics. In other embodiments, however, the liner 232 may he composed of other suitable materials.

Downstream of the feedstock injector section 230, the feedstock mixer section 240 is configured to receive a mixture of the carrier gas 209 and the feedstock gas 236 at a generally supersonic speed. The transfer of enthalpy from the carrier gas 209 to the feedstock gas 235 has been generally completed by the feedstock mixer section 240. Downstream of the feedstock mixer section 240, the supersonic mixture of the carrier and feedstock gases enters the supersonic diffuser section 250. As the mixture of carrier and feedstock gases at supersonic velocity enters a contraction 245 of the supersonic diffuser section 250, the mixture decelerates through the contraction 245, which raises the temperature of the gases. In some embodiments of the present technology, the mixture decelerates to a near-sonic velocity (e.g., 1.1-1.2 M) at the minimum cross section of the supersonic diffuser section 250. The temperature increase that accompanies the deceleration of the gases promotes the pyrolysis of the feedstock gas which, in turn, decreases the temperature of the gases. In some embodiments of the present technology, the contraction 245 may be designed such that these temperature-increasing and temperature-decreasing effects mostly or completely cancel out, resulting in a generally isothermal flow of the gases through the contraction 245. Generally, different olefin fractions are synthesized at different temperatures. For example, a temperature range of about 1600-1800 K promotes a synthesis of acetylene ($C_2H_2$) and a short residence time, while a temperature range of about 1000-1100 K and a longer residence time promotes a synthesis of ethylene ($C_2H_4$). Therefore, a design of the contraction section (e.g., how quickly its cross-section shrinks in the downstream direction) can he used to select a preferred olefin fraction by setting the isothermal temperature of the gases in the flow to promote the relevant pyrolytic reaction.

The mixture of carrier gas, olefins, and remaining feedstock gas decelerates from a supersonic to a subsonic flow while passing through a normal shock wave train 251 that promotes mixing of the gases and increases their temperature. This increase in temperature promotes pyrolysis of the remaining feedstock. After flowing through the normal shock wave train 251, the gases include olefins, carrier gas, and remaining unreacted feedstock. In some embodiments of the present technology, about 60-90% of the olefin production can take place at supersonic velocity, while the remaining 10-40% of the olefin production is completed at subsonic velocity (as contrasted with conventional shock wave reactors having about 0-5% of the pyrolytic reaction at supersonic velocity and 95-100% at subsonic velocity). In some embodiments, the gases leaving the supersonic diffuser section 250 can be routed to a heat exchanger (not shown) to reduce the temperature of the gases and to arrest chemical reactions. In other embodiments the gases leaving the the supersonic diffuser section 250 can be cooled by injecting a quench fluid such as water or a hydrocarbon.

Figure 3:
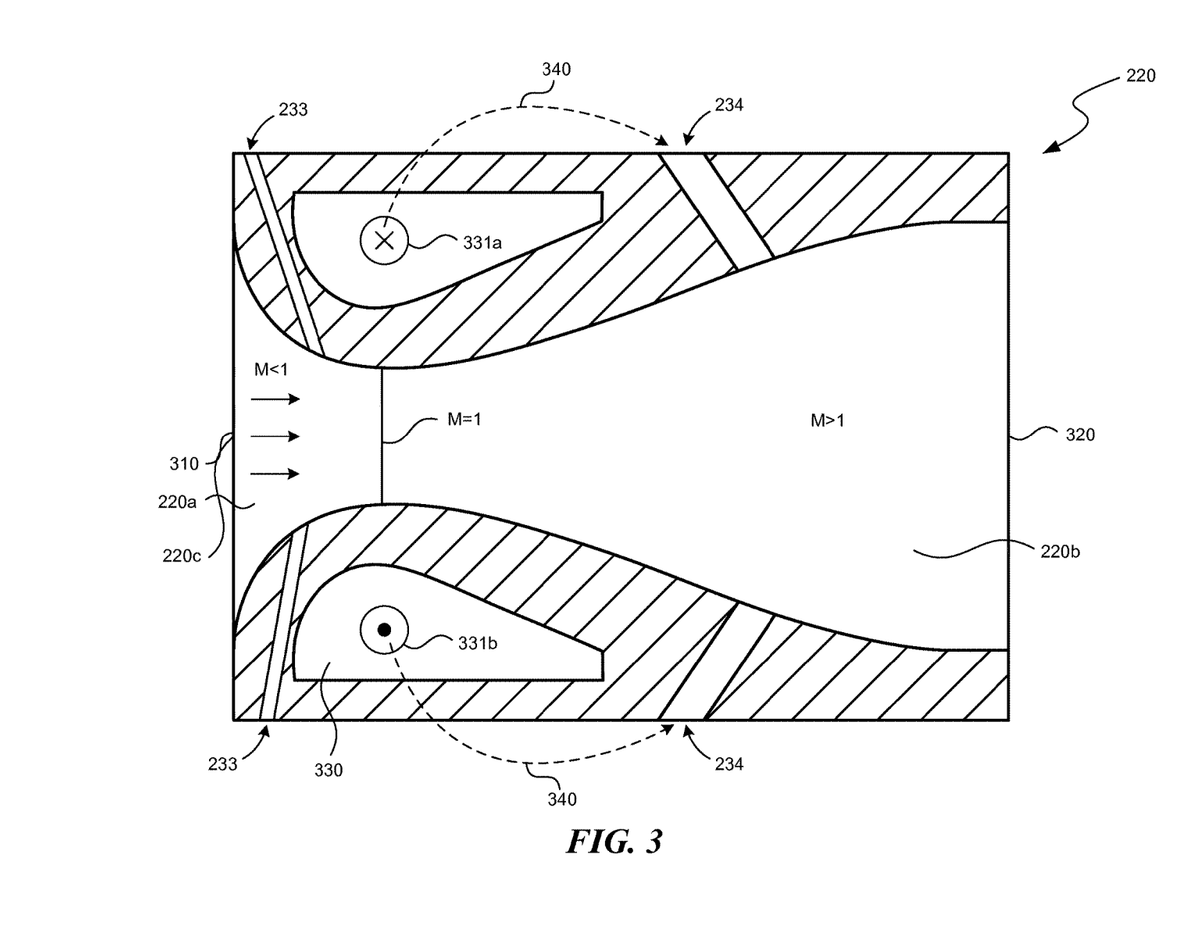
FIG. 3 is an enlarged cross-sectional view of the convergent-divergent nozzle of the reactor of FIG. 2.

FIG. 3 is an enlarged cross-sectional view of the convergent-divergent nozzle 220 of the olefin reactor 200 of FIG. 2. Generally, in operation the carrier gas enters the convergent-divergent nozzle 220 at an inlet 310 at a subsonic velocity, and then accelerates as it flows axially through the convergent-divergent nozzle 220. At an outlet 320 of the convergent-divergent nozzle 220, the carrier gas flows at a supersonic velocity (M>1). As explained above with reference to FIG. 2, in some embodiments the feedstock gas can be added into the convergent-divergent nozzle 220 through the nozzle injector(s) 234. Adding feedstock gas into the convergent-divergent nozzle 220 is expected to be beneficial because the flow is not yet at its ultimate Mach number (i.e., not fully expanded and accelerated) and, therefore, pressure losses associated with the introduction of the feedstock gas into the convergent-divergent nozzle 220 are smaller as compared with systems in which the feedstock gas is added to a fully expanded and accelerated flow downstream of the convergent-divergent nozzle 220. Transition from subsonic flow at the inlet 310 to supersonic flow at the outlet 320 is accompanied by heating of the convergent-divergent nozzle 220. Therefore, in some embodiments, the convergent-divergent nozzle 220 can be cooled using, e.g., feedstock gas, water, steam, or hydrogen. For example, the convergent-divergent nozzle 220 may be configured such that the feedstock gas circulates around the throat 220c. As shown in FIG. 3, for example, numeral 331a represents flow of the feedstock gas in the direction of the paper and the numeral 331b represents flow of the feedstock gas out of the paper. In other embodiments, however, the feedstock gas may have a different flow arrangement relative to the throat 220c. In some embodiments, preheated feedstock gas can be fed into the nozzle injectors 234 (FIG. 2), thereby improving the overall energy efficiency of the process. The flow of the preheated feedstock gas into the nozzle injectors 234 is schematically illustrated by dashed line 340. In other embodiments, water, steam, or hydrogen may be injected through cooling film injectors 233 for film cooling of the throat of the convergent-divergent nozzle 220.

Figure 4:
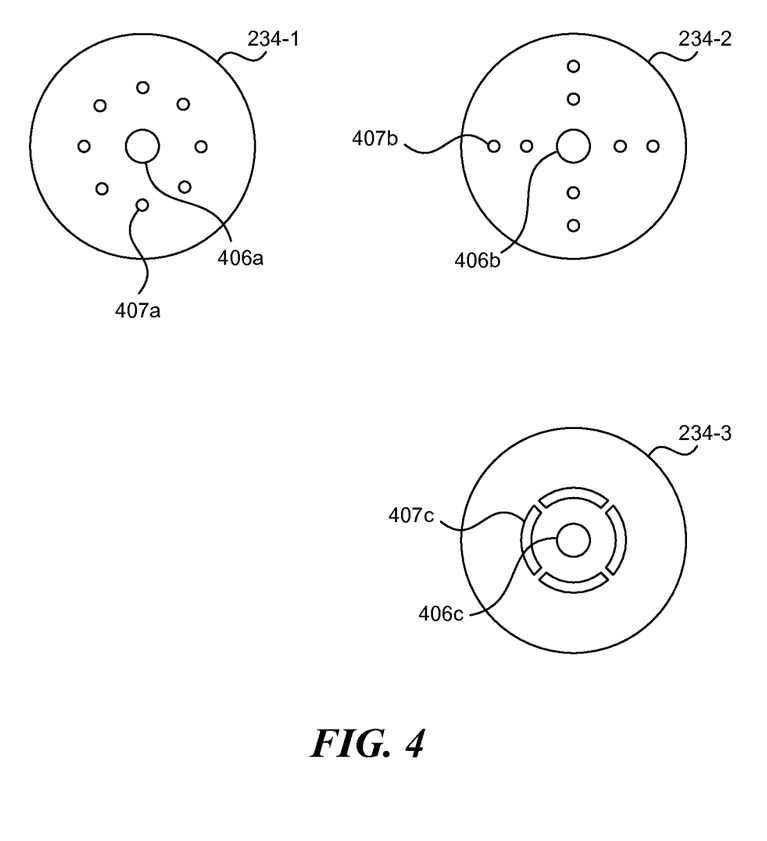
FIG. 4 is a plan view of several embodiments of injectors for the feedstock gas in the expanding section of the nozzle configured in accordance with the present technology.

FIG. 4 is a plan view of several different embodiments of the nozzle injectors configured in accordance with the present technology when viewed from the inside of the divergent section 220b of nozzle 220. In one embodiment, for example, a nozzle injector 234-1 includes a central opening 406a for injecting the carrier gas and several additional openings 407a that are concentric with the central opening 406a for injecting the feedstock gas. In at least some embodiments, such distribution of the openings may further promote mixing of the feedstock and carrier gases. In another example, injector 234-2 includes the central opening 406b for the carrier gas and the additional openings 407b for the feedstock gas arranged generally orthogonal to each other about the central opening 406b. In yet another example, an injector 234-3 includes the central opening 406c for the carrier gas and angular openings 407c for the feedstock gas concentric with the central opening 406c. In still further embodiments, the injector 234 may have other arrangements and/or features.

Figure 5:
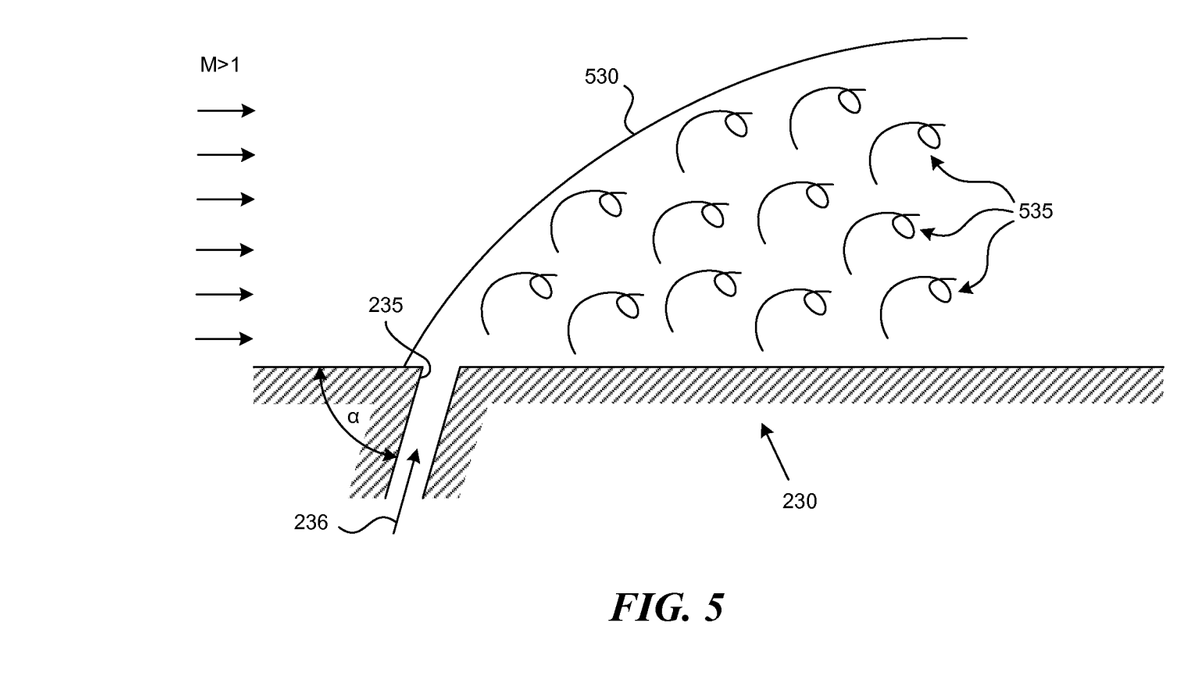
FIG. 5 is an enlarged, partially schematic cross-sectional view of the feedstock gas injector of FIG. 2 configured in accordance with an embodiment of the present technology.

FIG. 5 is an enlarged, partially schematic cross-sectional view of the feedstock gas injector 235 of FIG. 2 configured in accordance with an embodiment of the present technology. In the illustrated embodiment, the carrier flow approaches the feedstock injector 235 at a velocity M>1. The feedstock gas 236 can be introduced to the flow of the carrier gas at an angle α (an acute angle) to reduce pressure losses in the carrier flow. Introduction of the feedstock gas 236 into the carrier flow produces plumes 535 that contain a mixture of the carrier gas and the feedstock gas. Boundary line 530 is shown for illustrative purposes to denote the boundary between a flow region of predominantly carrier gas and a flow region having the plumes 535 and also to indicate the existence of a bow shock generated by the feedstock plume. The interaction of the plumes 535 and downstream feedstock injectors is explained in more details below with reference to FIGS. 6 and 7.

Figure 6:
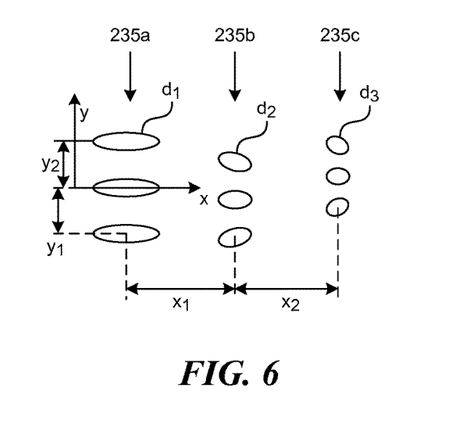
FIGS. 6 and 7 schematically illustrate layout of the feedstock injectors configured in accordance with an embodiment of the present technology.
Figure 7:
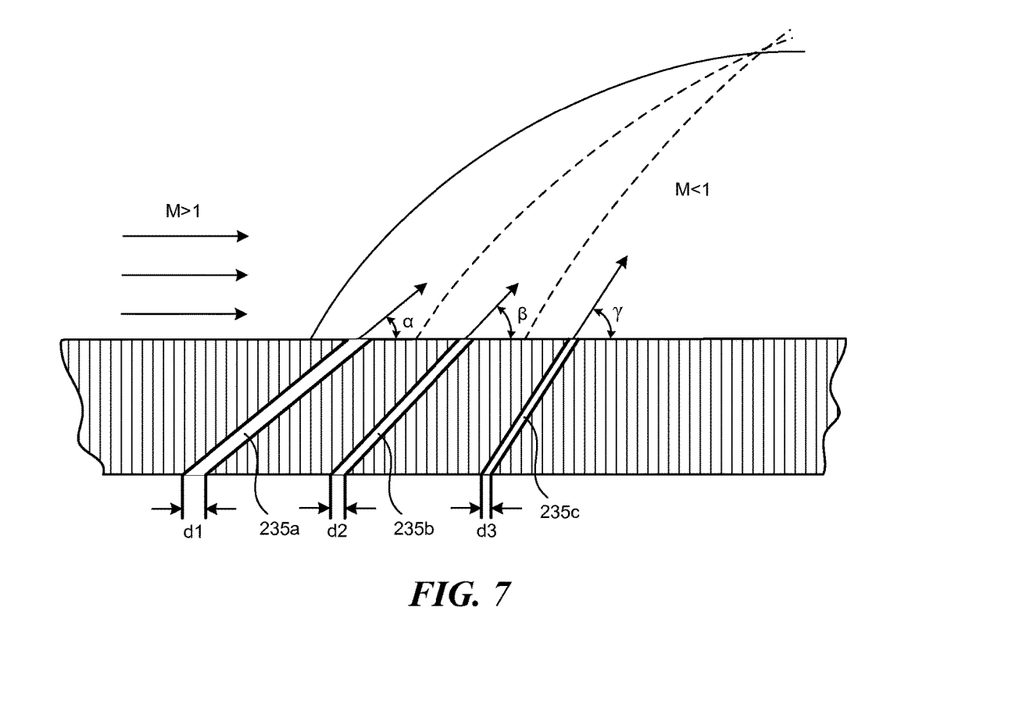

FIGS. 6 and 7 schematically illustrate a layout of the feedstock injectors 235a-235c of FIG. 2 in accordance to an embodiment of the present technology. The layout of the feedstock injectors is designated by $y_1$ and $y_2$ in a vertical direction and by $x_1$ and $x_2$ in a horizontal direction. The $y_1$, $y_2$ and/or $x_1$, $x_2$ can be selected to promote better mixing of the carrier gas and the feedstock gas and to minimize pressure losses as the feedstock gas enters the feedstock injector section. For example, the feedstock injectors 235a can be at generally different "y" locations than the feedstock injectors 235b and/or 235c (staggered layout). In at least some embodiments, the staggered layout of the feedstock injectors may promote mixing of the carrier gas and feedstock gas and may also lower pressure losses at the more downstream feedstock injectors (e.g., 235b, 235c). In some embodiments, for example, the diameters of the feedstock injectors 235a-235c can be different, thus enabling better control of the feedstock flow into the feedstock injector section. FIG. 7 is an enlarged side cross-sectional view of the feedstock injectors 235a-235c. In at least some embodiments, the feedstock injectors 235a-235c can have different angles with respect to the direction of the carrier gas flow. For example, the most upstream feedstock injector 235a can introduce the feedstock gas at an angle α. The downstream feedstock injectors 235b and 235c can introduce the feedstock gas at angles β and γ, which are bigger than the angle α. The plumes created at the upstream feedstock injector 235a generally reduce the velocity of the supersonic flow, thus the feedstock gas can be introduced at relatively bigger angles of the feedstock injectors 235b and 235c without resulting in significant pressure losses.

EXAMPLES

1. A shock wave reactor, comprising:
    a feedstock injector section having an inlet for receiving a carrier gas at supersonic velocity;
    a first feedstock injector positioned to inject a feedstock gas into the feedstock injector section at a first angle with respect to a longitudinal axis of the feedstock injector section; and
    a second feedstock injector positioned to inject the feedstock gas into the feedstock injector section at a second angle with respect to the longitudinal axis of the feedstock injector section, wherein the second angle is greater than the first angle.

2. The reactor of example 1 wherein the second feedstock injector is positioned to inject the feedstock gas within a plume zone created by the first feedstock injector.

3. The reactor of example 1, further comprising a third feedstock injector positioned to inject the feedstock gas into the feedstock injector section at a third angle with respect to the longitudinal axis of the feedstock injector section, wherein the third angle is greater than the second angle.

4. The reactor of example 1 wherein the first and second feedstock injectors are generally aligned in a direction of the longitudinal axis.

5. The reactor of example 1 wherein the feedstock gas is injected at a supersonic velocity.

6. The reactor of example 1 wherein velocity of the carrier gas is greater than Mach 2.

7. The reactor of example 1 wherein the feedstock injectors are configured and positioned to introduce about 50% of a total gas flow through the reactor.

8. The reactor of example 1, further comprising a supersonic mixer section downstream of the feedstock injector section, wherein, during operation, oblique shock waves develop in the supersonic mixer section such that the carrier gas and the feedstock gas react in the supersonic mixer section at least partially at a thermal cracking point.

9. The reactor of example 1, further comprising a layer of thermally protective coating over at least a portion of an inner surface of the feedstock injector section.

10. The reactor of example 1, further comprising a convergent-divergent nozzle configured to accelerate the carrier gas from subsonic velocity to supersonic velocity.

11. The reactor of example 10 wherein the convergent-divergent nozzle comprises a nozzle injector positioned to inject at least one of the feedstock gas and the carrier gas.

12. The reactor of example 10, further comprising a cooling film injector positioned in a convergent section of the convergent-divergent nozzle.

13. The reactor of example 11 wherein the nozzle injector is positioned in a divergent section of the convergent-divergent nozzle.

14. The reactor of example 11, further comprising a cooling channel around a throat of the convergent-divergent nozzle, wherein the cooling channel is configured to receive the feedstock gas.

15. The reactor of example 1 wherein the feedstock injector comprises a liner for reducing catalytic wall effects.

16. The reactor of example 1, further comprising a supersonic diffuser section configured to decelerate flow from a supersonic to a near-sonic velocity at a minimum cross section of the supersonic diffuser section.

17. The reactor of example wherein the feedstock gas comprises methane.

18. The reactor of example 16 wherein the supersonic diffuser section comprises a contraction configured to decelerate the feedstock gas and to keep the feedstock gas generally isothermal.

19. The reactor of example 1, further comprising a combustor for generating a carrier gas from a mixture of a fuel and an oxydizer.

20. The reactor of example 1, wherein the fuel is selected from a group consisting of a methane, a hydrogen, and a combination thereof.

21. The reactor of example 1, wherein he oxydizer comprises oxygen.

22. The reactor of example 16 wherein an expanding section of the supersonic diffusion section is configured to stabilize a normal shock wave train.

23. The reactor of example 22 wherein the normal shockwave train is configured to generate thermal cracking point for the feedstock gas.

24. A method of synthesizing gases, the method comprising:
accelerating a carrier gas flow from subsonic to supersonic velocity in a convergent-divergent nozzle, wherein the supersonic velocity predominates at an entrance to a feedstock injector section;
adding a feedstock gas to the feedstock injector section through a first feedstock injector at a first angle with respect to a longitudinal axis of the feedstock injector section;
adding the feedstock gas to the feedstock injector section through a second feedstock injector at a second angle with respect to the longitudinal axis of the feedstock injector section, wherein the second angle is greater than the first angle, and wherein the second feedstock injector is positioned to inject the feedstock gas a plume zone created by the first feedstock injector, wherein the carrier gas reacts with the feedstock gas to generate olefins; and wherein a mixture of the carrier gas, the feedstock gas and the olefins decelerates from the supersonic to the subsonic velocity in a supersonic diffuser section.

25. The method of example 24 wherein the feedstock gas reacts predominantly in a supersonic mixer section and a contraction of the supersonic diffuser section positioned downstream of the feedstock injector section.

26. The method of example 25 wherein the feedstock gas continues to react in through a normal shock wave train of the supersonic diffuser section.

27. The method of example 25, further comprising:
maintaining the feedstock gas at generally isothermal condition in the contraction of the supersonic diffuser section.

28. The method of example 24, further comprising:
adding the feedstock gas to the feedstock injector section through a third feedstock injector at a third angle with respect to the longitudinal axis of the feedstock injector section, wherein the third angle is greater than the second angle, and wherein the third feedstock injector is positioned to inject the feedstock gas within a plume zone created by the first and the second feedstock injectors.

29. The method of example 24, further comprising:
preheating the feedstock gas by flowing the feedstock gas through a cooling channel around a throat of the convergent-divergent nozzle.

30. The method of example 24, further comprising:
film cooling the convergent-divergent nozzle by injecting at least one of the steam, water, and hydrogen upstream of the throat of the convergent-divergent nozzle.

31. The method of example 24, further comprising:
initiating an auto-ignited reaction between a fuel and an oxidizer to form the carrier gas in a combustor section upstream of the feedstock injector.

32. The method of example 31, further comprising:
preheating di-ether and oxygen to an auto-ignition temperature;
mixing di-ether and oxygen to initiate an auto-ignition reaction; and
forming the carrier gas using the auto-ignition reaction as a pilot.

33. The method of example 24 wherein the feedstock gas comprises me a

The above detailed descriptions of embodiments of the technology are not intended to be exhaustive or to limit the technology to the precise form disclosed above. Although specific embodiments of, and examples for, the technology are described above for illustrative purposes, various equivalent modifications are possible within the scope of the technology, as those skilled in the relevant art will recognize. Further, while steps are presented in a given order, alternative embodiments may perform steps in a different order. The various embodiments described herein may also be combined to provide further embodiments.

From the foregoing, it will be appreciated that specific embodiments of the technology have been described herein for purposes of illustration, but well-known structures and functions have not been shown or described in detail to avoid unnecessarily obscuring the description of the embodiments of the technology. Where the context permits, singular or plural terms may also include the plural or singular term, respectively.

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the technology. Further, while advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

We claim:

1. A shock wave reactor, comprising:
a feedstock injector section having an inlet for receiving a carrier gas at supersonic velocity;
a first feedstock injector positioned to inject a first stream of a feedstock gas into the feedstock injector section at a first acute angle with respect to a longitudinal axis of the feedstock injector section; and a second feedstock injector positioned to inject a second stream of the feedstock gas into the feedstock injector section at a second acute angle with respect to the longitudinal axis of the feedstock injector section, wherein the second acute angle is greater than the first acute angle.

2. The reactor of example 1 wherein the second feedstock injector is positioned to inject the second stream of the feedstock gas within a plume zone created by the first feedstock injector.

3. The reactor of example 1, further comprising a third feedstock injector positioned to inject a third stream of the feedstock gas into the feedstock injector section at a third acute angle with respect to the longitudinal axis of the feedstock injector section, wherein the third acute angle is greater than the second acute angle.

4. The reactor of claim 1 wherein the first and second feedstock injectors are generally aligned in a direction of the longitudinal axis.

5. The reactor of claim 1 wherein the first and second streams of the feedstock gas are injected at a supersonic velocity.

6. The reactor of claim 1 wherein velocity of the carrier gas is greater than Mach 2.

7. The reactor of claim 1 wherein the feedstock injectors are configured and positioned to introduce about 50% of a total gas flow through the reactor.

8. The reactor of claim 1, further comprising a supersonic mixer section downstream of the feedstock injector section, wherein, during operation, oblique shock waves develop in the supersonic mixer section such that the carrier gas and the feedstock gas react in the supersonic mixer section at least partially at a thermal cracking point.

9. The reactor of claim 1, further comprising a layer of thermally protective coating over at least a portion of an inner surface of the feedstock injector section.

10. The reactor of claim 1, further comprising a convergent-divergent nozzle configured to accelerate the carrier gas from subsonic velocity to supersonic velocity.

11. The reactor of claim 10 wherein the convergent-divergent nozzle comprises a nozzle injector positioned to inject at least one of the feedstock gas and the carrier gas.

12. The reactor of claim 11 wherein the nozzle injector is positioned in a divergent section of the convergent-divergent nozzle.

13. The reactor of claim 11, further comprising a cooling channel around a throat of the convergent-divergent nozzle, wherein the cooling channel is configured to receive the feedstock gas.

14. The reactor of claim 10, further comprising a cooling film injector positioned in a convergent section of the convergent-divergent nozzle.

15. The reactor of claim 1 wherein the feedstock injector comprises a liner for reducing catalytic wall effects.

16. The reactor of claim 1, further comprising a supersonic diffuser section configured to decelerate flow from a supersonic to a near-sonic velocity at a minimum cross section of the supersonic diffuser section.

17. The reactor of claim 16 wherein an expanding section of the supersonic diffusion section is configured to stabilize a normal shock wave train.

18. The reactor of claim 17 wherein the normal shock wave train is configured to generate thermal cracking point for the feedstock gas.

19. The reactor of claim 1 wherein the feedstock gas comprises methane.

20. The reactor of claim 19 wherein the supersonic diffuser section comprises a contraction configured to decelerate the feedstock gas and to keep the feedstock gas generally isothermal.

21. The reactor of claim 1, further comprising a combustor for generating a carrier gas from a mixture of a fuel and an oxydizer.

22. The reactor of claim 21, wherein the fuel is selected from a group consisting of a methane, a hydrogen, and a combination thereof.

23. The reactor of claim 21, wherein the oxydizer comprises oxygen.

24. A method of synthesizing gases, the method comprising:
accelerating a carrier gas flow from subsonic to supersonic velocity in a convergent-divergent nozzle, wherein the supersonic velocity predominates at an entrance to a feedstock injector section;
adding a first stream of a feedstock gas to the feedstock injector section through a first feedstock injector at a first acute angle with respect to a longitudinal axis of the feedstock injector section;
adding a second stream of the feedstock gas to the feedstock injector section through a second feedstock injector at a second acute angle with respect to the longitudinal axis of the feedstock injector section, wherein the second acute angle is greater than the first acute angle, wherein the second feedstock injector is positioned to inject the second stream of the feedstock gas within a plume zone created by the first feedstock injector, wherein the carrier gas reacts with the feedstock gas to generate olefins; and wherein a mixture of the carrier gas, the feedstock gas and the olefins decelerates from the supersonic to the subsonic velocity in a supersonic diffuser section.

25. The method of claim 24 wherein the feedstock gas reacts predominantly in a supersonic mixer section and a contraction of the supersonic diffuser section positioned downstream of the feedstock injector section.

26. The method of claim 25 wherein the feedstock gas continues to react in through a normal shock wave train of the supersonic diffuser section.

27. The method of claim 25, further comprising:
maintaining the feedstock gas at generally isothermal condition in the contraction of the supersonic diffuser section.

28. The method of claim 24, further comprising:
adding a third stream of the feedstock gas to the feedstock injector section through a third feedstock injector at a third acute angle with respect to the longitudinal axis of the feedstock injector section, wherein the third acute angle is greater than the second acute angle, and wherein the third feedstock injector is positioned to inject the third stream of the feedstock gas within a plume zone created by the first and the second feedstock injectors.

29. The method of claim 24, further comprising:
preheating the feedstock gas by flowing the feedstock gas through a cooling channel around a throat of the convergent-divergent nozzle.

30. The method of claim 24, further comprising:
film cooling the convergent-divergent nozzle by injecting at least one of the steam, water, and hydrogen upstream of the throat of the convergent-divergent nozzle.

31. The method of claim 24, further comprising:
initiating an auto-ignited reaction between a fuel and an oxidizer to form the carrier gas in a combustor section upstream of the feedstock injector.

32. The method of claim 31, further comprising:
preheating di-ether and oxygen to an auto-ignition temperature;
mixing di-ether and oxygen to initiate an auto-ignition reaction; and
forming the carrier gas using the auto-ignition reaction as a pilot.

33. The method of claim 24 wherein the feedstock gas comprises methane.

* * * * *